United States Patent [19]

Franke

[11] Patent Number: 4,504,858

[45] Date of Patent: Mar. 12, 1985

[54] X-RAY DIAGNOSTIC SYSTEM FOR ANGIOGRAPHIC X-RAY EXAMINATIONS

[75] Inventor: Kurt Franke, Erlangen, Fed. Rep. of Germany

[73] Assignee: Siemens Aktiengesellschaft, Berlin & Munich, Fed. Rep. of Germany

[21] Appl. No.: 424,458

[22] Filed: Sep. 27, 1982

[30] Foreign Application Priority Data

Dec. 8, 1981 [DE] Fed. Rep. of Germany ....... 3148507

[51] Int. Cl.³ ............................................. H04N 5/32
[52] U.S. Cl. ...................................... 358/111; 378/99
[58] Field of Search .......................... 358/111; 378/99; 128/653, 654

[56] References Cited

U.S. PATENT DOCUMENTS

| 4,204,225 | 5/1980 | Mistretta | 358/111 |
| 4,204,226 | 5/1980 | Mistretta | 358/111 |
| 4,393,402 | 7/1983 | Keyes | 378/99 |

Primary Examiner—John C. Martin
Assistant Examiner—Edward L. Coles
Attorney, Agent, or Firm—Hill, Van Santen, Steadman & Simpson

[57] ABSTRACT

An X-ray diagnostic system for angiographic X-ray examinations having an X-ray source for irradiating a patient, a television image intensification chain, a digital semiconductor memory for storing image data and an image subtraction device for producing images which are the result of the difference between images taken with the patients injected with an X-ray contrast medium and images taken without the X-ray contrast medium. The resulting subtraction image shows only the blood vessels important to the examination. A control device directs the storage of data in the digital semiconductor memories. The memories contain data for successive images and, when full, may be overwritten by subsequent image data.

3 Claims, 3 Drawing Figures

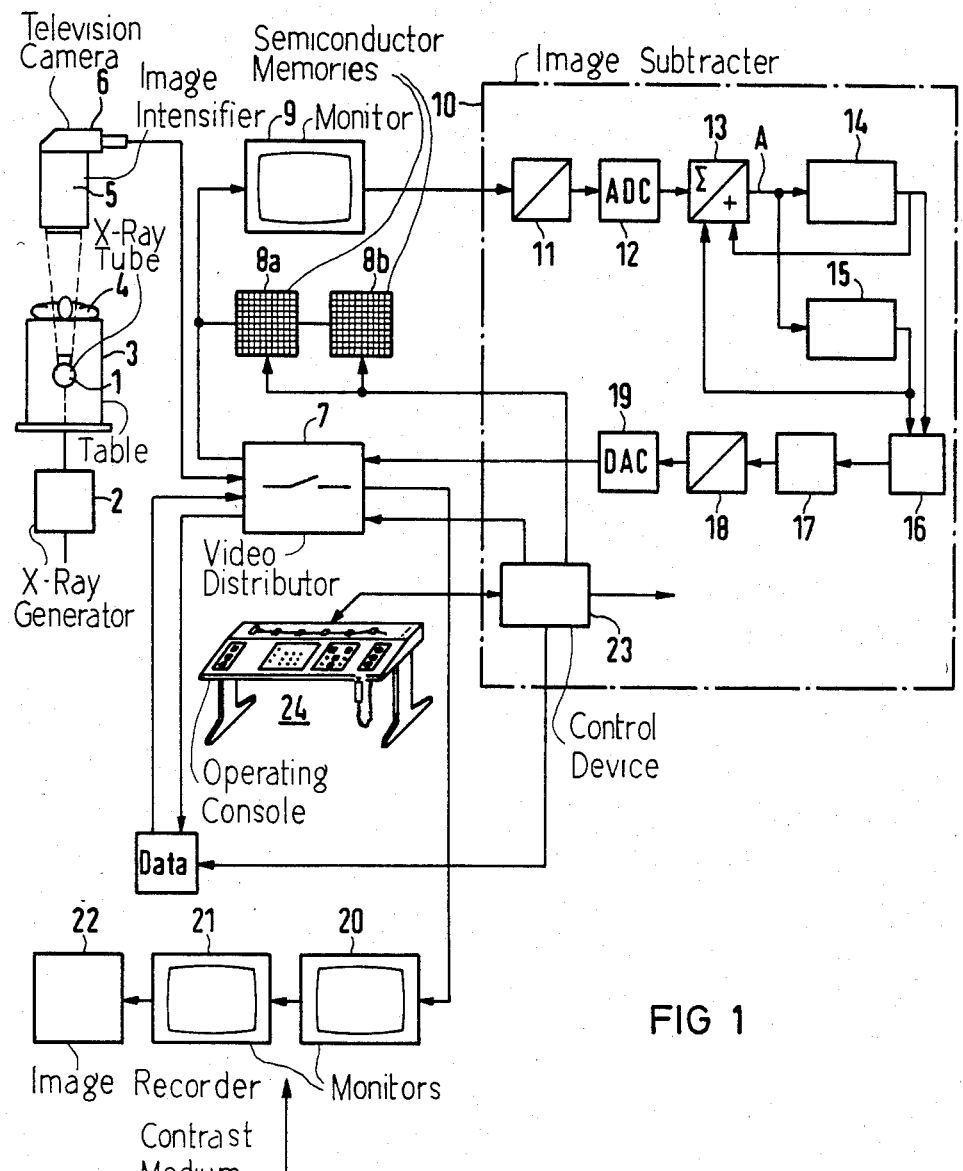

X-RAY DIAGNOSTIC SYSTEM FOR ANGIOGRAPHIC X-RAY EXAMINATIONS

BACKGROUND OF THE INVENTION

1. Field of the Invention

The present invention relates to X-ray diagnostic systems, and in particular, to such systems for angiographic examinations employing an image intensifier television chain, an image substraction device with at least one image memory whose image data are subtracted from image data taken at times other than the stored image data, and devices for displaying and recording successive television subtraction images.

2. Description of the Prior Art

An X-ray diagnostic system is described in German patent application No. P 31 22 098.3. That system includes an image memory in which can be stored a single X-ray image, or several integrated X-ray images, obtained prior to subjecting the radiography patient to an injection of an X-ray contrast medium. Such an image is known as a blank image. After injection of the contrast medium, an image known as a filling image is taken of the same region as the blank image. The blank image is subtracted from the filling image, thereby producing a real-time fluoroscope image showing only the blood vessels important to the diagnosis.

Also in that system, a video tape recorder is provided for storing individual images takes so that the image subtraction may later be performed on the basis of a selected stored tape. To do this, however, it is necessary to seek and find specific locations on the tape. This can be inconveniently time consuming. Furthermore, the analog storage of the picture signals on the tape is associated with a loss of image quality.

SUMMARY OF THE INVENTION

It is an object of the present invention to provide an X-ray diagnostic system for angiographic examination capable of storing image takes with increased stored image quality and reduced access time to specific stored images.

The above object is inventively achieved by providing an image take storage device which comprises at least one digital semiconductor memory. The invention further provides a control device operatively associated with the memory. The memory has a capacity to store a number of successive television images. When the memory addresses of the semiconductor memory are filled, previously stored image takes are overwritten, beginning with the first filled memory address.

According to important features of the invention, the digital semiconductor memory for storing X-ray images takes has an extremely fast access time and improved image quality as compared to video tape storage. In the semiconductor memory, a section of the entire X-ray take may be stored. This section may be placed so that it contains the images desired by the examining individual.

According to another important feature of the invention, two or more digital semiconductor memories can be connected in series for increased image take storage capacity.

By providing an image subtractor, the present invention enables the examining individual to take successive X-ray images at time intervals during which an X-ray contrast medium progresses through a patient's vessels, to substract various selected images, some of which can be stored and retrieved rapidly and selectively in the semiconductor memory, and to display the image resulting from the subtraction, which will show only the important vessels.

Other features and objects of the invention will become apparent from the following detailed description of a preferred embodiment, taken with the accompanying drawings.

BRIEF DESCRIPTION OF THE DRAWINGS

FIG. 1 is a schematic drawing of an X-ray diagnostic system constructed in accordance with the principles of the invention;

FIG. 2 is a graph representing the blood vessel X-ray contrast medium concentration over time; and FIG. 3 is a graph representing the sequence of image take storage in a digital semiconductor memory.

DESCRIPTION OF THE PREFERRED EMBODIMENT

The X-ray diagnostic system illustrated in FIG. 1 has an X-ray source including an X-ray tube 1 which is fed by an X-ray generator 2 for irradiating a patient 4 lying on an X-ray table 3. An image intensifier television chain, including an X-ray image intensifier 5 and a television camera 6, receives the X-ray images and converts them into a video signal which is supplied to a video distributor 7 which directs the storage of the X-ray images of individual examined takes into two digital semiconductor memories 8a and 8b and controls the display of the stored images on a monitor 9.

In the formation of difference images, the video signal is supplied either in real time or delivered by the semiconductor memories 8a and 8b to an image subtraction device 10. In the general organization of this image subtracter, at the input there is a logarithmizer 11, the output signal of which is passed to an analog-to-digital converter 12. The logarithmizer 11 causes signals to be subtracted from one another, the signals being proportional to the sum of the products of mass attenuation coefficient and mass of all substances which lie in the ray trace. In series with the output of the analog to digital converter 12, there is a mean value formation element 13 which performs a sliding, weighted mean value information for the purpose of signal-to-noise ratio improvement. The mean value formation element 13 may also perform a summation of image signals. The thus-obtained image signals are stored in two subtracter image memories 14 and 15, which are in turn connected to a subtracter 16 whose output signal, via a window amplifier 17, a delogarithmizer 18, and a digital-to-analog converter 19, is supplied to the video distributor 7, which effects the display of the subtraction images on monitors 20 and 21. With the aid of an image recording device 22, the subtraction images can be permanently retained, such as by photography.

As a first step in the production of angiographic subtraction images, the patient is irradiated subsequent to injection of a contrast medium into a blood vessel but before the contrast medium has spread in the vessel region to be examined. A mask is placed in the subtracter image memory 14 which corresponds to the averaging or integration of several blank images. Subsequently, preferably during the maximum concentration of contrast medium in the vessel region to be examined, an averaging or integration of several filling images is stored in the subtracter image memory 15. The contents of memory 14 is subtracted from the contents memory 15 by the subtracter 16, and subtraction images are displayed on the monitors 20 and 21, which show only the vessels filled with contrast medium without the constant background.

For overall control of the entire X-ray diagnostic system, a control device 23 is provided, which is activated by an operating console 24.

The operating sequence of the X-ray diagnostic system is explained in more detail with reference to FIG. 2. The graph shows an example of the chronological progression of the contrast medium concentration in a blood vessel. At time $t_1$, before the contrast medium injection, a blank image is taken and the mask for the storage of the blank image is placed in the subtracter image memory 14. The contrast medium injection begins at time $t_2$. At time $t_3$, a filling image is taken and its mask is placed in the subtracter image memory 15. Preferably, time $t_3$ corresponds to the maximum concentration of contrast medium.

FIG. 3 graphically illustrates this sequence of storage of the television image series in the digital semiconductor memory 8a. For purposes of explanation, it is assumed that there is only a single semiconductor memory present; i.e., the semiconductor memory 8b is not present. During the time period represented by a bar 25, a series of television images is stored in the semiconductor memory 8a. When all the memory addresses of semiconductor memory 8a are full, storage of further television images proceeds by overwriting the memory commencing with the first filled address of semiconductor memory 8a. The change to overwriting is represented by bar 26. The storage of image data can be stopped when the desired television images needed by the examining individual are stored in the semiconductor memory 8a.

The semiconductor memory 8b is provided to expand the memory capacity. It is connected in series with the semiconductor memory 8a so that the memory capacity is doubled as compared to the use of only one semiconductor memory. In operation, the addresses of memory 8a would be filled first, than those of memory 8b. When memory 8b is filled, an overwriting of the image data commences with the first memory location of the semiconductor memory 8a. This overwriting is ceased when the desired image take is stored.

It is advantageous to sequence operation so that the storage process represented by bar 25 corresponds to the time interval from $t_0$ to $t_2$. In this manner, the semiconductor memories 8a and 8b will store an image sequence which contains the significant data of several blank images and several filling images. The stored data in memories 8a and 8b may then be used to construct the blank image and substractor image memory 14 and the filling image in substractor image memory 15.

To provide even greater image data storage capacity, three or more semiconductor memories may be connected in series with the data successively stored and overwritten through the semiconductor memories.

For improved utilization of the memory capacity, it is advantageous to use the control device 23 to switch off the semiconductor memories 8a and 8b during periods of unimportant images. The control device 23 can also be used to cause two or more individual images to be summed up on one memory location of the semiconductor memories 8a and 8b. This results in improved utilization of the memory capacity and increase in take time. Furthermore, quantum noise is reduced.

Although modifications and changes may be suggested by those skilled in the art, it is the intention of the inventor to embody within the patent warranted hereon all changes and modifications as reasonably and properly come within the scope of his contribution to the art.

I claim:

1. An X-ray diagnostic system for angiographic X-ray examinations comprising:
   an X-ray source means;
   an image intensifier television chain having an output for supplying a succession of output image data representing successive images;
   a patient support means disposed between said X-ray source means and said image intensifier television chain;
   digital semiconductor memory means for storing said output image data from said image intensifier television chain beginning at a first memory location;
   image subtraction device means having at least one image memory for storing image data which is to be subtracted from image data taken at times other than the times of the image data stored by said one image memory, said one memory storing a complete image so as to produce subtraction images which are the result of a subtraction between image data in said one image memory and the image data taken at other times;
   control device means operatively associated with said digital semiconductor means for controlling the storage of said output image data representing successive images in said digital semiconductor memory means such that when the memory locations of said digital semiconductor memory means are filled with image data, the stored image data is successively overwritten commencing at the first memory location; and
   display means connected with said image subtraction device means for displaying said subtraction images;
   said digital semiconductor memory means being coupled with said image intensifier television chain in advance of said one image memory of said image substraction device means such that image data stored by said digital semiconductor memory means can be selectively supplied to said one image memory of said image subtraction device means.

2. The X-ray diagnostic system of claim 1, wherein said control device means causes successive image data to be summed at the memory locations of said digital semiconductor memory means.

3. The X-ray diagnostic system of claim 1, wherein said control device means causes said digital semiconductor memory means to be turned off during unimportant images.

* * * * *